United States Patent [19]

Meierhenry

[11] 4,055,660
[45] Oct. 25, 1977

[54] TREATMENT FOR WARTS

[76] Inventor: Dwight W. Meierhenry, 738 E. Sahara Ave., Las Vegas, Nev. 89104

[21] Appl. No.: 704,285

[22] Filed: July 12, 1976

Related U.S. Application Data

[63] Continuation-in-part of Ser. No. 483,681, June 26, 1974, abandoned.

[51] Int. Cl.$^2$ .......................................... A61K 31/245
[52] U.S. Cl. ..................................... 424/310; 424/330
[58] Field of Search .......................................... 424/310

[56] References Cited

PUBLICATIONS

Wilson, et al., Textbook of Organic Medicinal and Pharmaceutical Chemistry, 4th Edition, (1962), pp. 520-522.

Sadik, Handbook of Non-Prescription Drugs, (1973), pp. 180-183.
The Merck Manual, (1972), 12th Edition, pp. 1436-1438.
The Merck Manual, 10th Edition, pp. 1444-1446.
Goodman et al., 3rd Edition, Pharmacological Basis of Therapeutics, pp. 378-385, (1965).

*Primary Examiner*—Leonard Schenkman
*Attorney, Agent, or Firm*—Edward J. Quirk

[57] ABSTRACT

Warts are resolved by peripheral injection of an aqueous procaine solution into and around one of the warts. A few weeks after injection, a reaction occurs around the base of the wart, and after a few months, the treated wart and other warts on the body diminish and slough off. The procaine solution is acidic and preferably contains a vasoconstrictor.

4 Claims, No Drawings

TREATMENT FOR WARTS

CROSS-REFERENCE TO RELATED APPLICATION

This application is a continuation-in-part of application Serial No. 483,681, filed June 26, 1974, now abandoned.

BACKGROUND OF THE INVENTION

Warts, or verrucae, are a common and troublesome occurrence of viral etiology. Their epidemiology is not well understood. In many cases partial or complete remission occurs over a period of months or years, however many cases refuse to resolve spontaneously.

The folklore concerning the etiology of warts is exceeded only by that relating to cures. Even recent credible medical publications report cures which are quite empirical and mysterious. For example, in the American Journal of Obstetrics & Gynecology, Vol. 116, p. 887, July 15, 1973, a doctor reports the cure of an extremely severe case of vulvar warts with hypnosis. Successful use of hypnosis in the treatment of warts, along with a literature review, is also reported by a group of doctors in Arch. Gen. Psychiatry, Vol. 2B, p 439ff, March 1972. An article in Practitioner, Vol 210, p 829, June 1973, prescribes exercises of the hip, lower leg, and foot for the cure of plantar warts. An article in Physical Therapy, Volume 53, p 396, April, 1973 summarizes the literature on treatment of plantar warts with ultrasound, and compares direct ultrasonic treatment with underwater ultrasonic treatment. The exposure of warts to x-rays in a well-known attempted cure, although serious radiation damage is a risk as reported by the Singapore Medical Journal, Vol 14, No 1, p 19, March, 1973.

Plantar warts, so characterized because they are found on the sole of the foot, are particularly painful and stubborn, and are the subject of many cure efforts. The successful surgical removal of plantar warts with a blunt instrument is described in Archives of Dermatology, Vol 108, p 79, July, 1973. An interesting procedure for treating recalcitrant plantar warts by sensitization of the patient to dinitrochlorobenzene, followed by topical treatment of the wart with a dinitrochlorobenzene solution, is reported in Journal of the American Podiatry Association, Vol 63, No 7, p 293, July, 1973. Other well-known methods for treating warts include curretage, dessication, electric cutting, freezing with carbon dioxide or liquid nitrogen, and treatment with salicylic acid, podophyllin resin, formaldehyde, bichloracetic acid, silver nitrate, linseed oil, and cantharidin.

Despite substantial effort, a satisfactory cure for warts has not been found. Although some of the treatments mentioned above are statistically quite effective, none are completely effective, and many are painful, dangerous and leave unacceptable scars. In addition, even after removal by these methods, warts frequently recur at original or new sites and must be retreated.

The treatment of the invention involves the injection of procaine directly into and under a wart. Procaine is the diethylaminoethyl ester of para-aminobenzoic acid, and has the following formula:

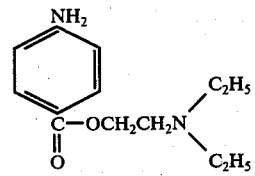

Sold under the trade names of Novocain, Ethocaine, and Neocaine, a solution of the hydrochloride salt of procaine has been sold for many years as a local anesthetic, and has achieved wide use. Procaine is a white crystalline powder, slightly soluble in water, melting at about 60° C. The hydrochloride salt, however, is freely water-soluble. The solution is sold as a 2% solution of procaine in water, generally with a small amount of vasoconstrictor, with sufficient strong acid (usually HCl) added to reduce the solution pH to between 4 and 5. The salt procaine hydrocloride is formed at this pH, but readily dissociates at pH above 7. When the solution is injected into alkaline tissues, the alkaloidal base is liberated and penetrates the nerve fibers, causing anesthesia. Although a relatively weak anesthetic, procaine has a long history of safe use, and is essentially systemically non-toxic, being readily hydrolyzed in the tissues and detoxified in the liver. Amounts to 20 cc of the 2% procaine solution are commonly used in dentistry without ill effects. In recent years, procaine has been used in combination with other anesthetics, such as provocaine (2 diethylaminoethyl 4-aminopropoxylbenzonate) or tetracaine (p-butylaminobenzoyl-dimethylaminoethanol hydrochloride) for increased potency.

Although primarily known as an injected anesthetic, procaine has been reported to be useful for other related and non-related purposes. For example, McCrea, U.S. Pat. No. 2,105,197, issued Jan. 11, 1938, discloses the use of procaine as a topical anesthetic to reduce itching sensation. Dekker, U.S. Pat. No. 3,175,941, issued Mar. 30, 1965 shows procaine to be an active fungicide against powdery mildew on plants. Tulek, U.S. Pat. No. 2,539,848, issued Jan. 30, 1951 uses procaine as a raw material for the manufacture of procaine urea salicylate, useful in treating ulcers. In addition, recent newspaper articles have reported procaine-based drugs to be useful for anti-depressant and anti-aging activity in humans.

SUMMARY OF THE INVENTION

Warts are resolved by subcutaneous injection of a procaine solution around the periphery of at least one wart. A few months after the injection, all of the warts on the infected body disappear.

Accordingly, it is an object of the invention to treat warts in a simple, painless manner such that they are removed without leaving scars.

It is a further object of the invention to remove all of the warts on a patient's body by the treatment of only one or a few of the warts.

It is still a further object of the invention to provide a cure for warts which prevents their recurrence.

DETAILED DESCRIPTION OF THE INVENTION

The first problem in treating warts according to the invention is to determine which wart or warts should be injected. Although selection of a single key wart does not seem to be critical, best results are obtained by working with the largest and ugliest, or "seed" wart, on the body. Only one wart need be treated according to the invention in order to establish the required reaction; if the treatment is effective for the treated wart, all of the other warts on the body will also be removed. More than one wart may be treated if desired; injection of multiple warts could increase the probability that the necessary initial sensitization reaction would occur.

The procaine solution is then injected in the immediate vicinity of the wart. By "the immediate vicinity" is meant directly around the periphery of the wart, or underneath the wart, or directly into the wart, or a combination of all of these locations. Injection is accomplished with a conventional syringe in multiple locations into and around the periphery of the wart, and directly into the wart. The injection needle is inserted subderminally just underneath the wart from several locations around the wart, such that the solution is infiltrated directly below the wart, between the wart tissue and the surrounding skin tissue. As solution is injected, the wart raises up from the volume of solution injected, and the tissue beneath the wart turns white in color. Solution is also injected directly into the center of the wart. It is important that the wart be completely saturated with solution; the injection is made under considerable pressure, and should continue until solution spurts out from the wart. Injection into the wart must continue until part of the wart structure is physically destroyed and bleeding occurs. While the amount of the solution used may vary with the size of the wart to be treated, a suitable total amount is usually between 0.5 and 5.0 cc's of 2% procaine solution, preferably from 1 to 1.5 cc's. Larger amounts can be used especially for large animals, but are generally unnecessary; no problems with toxicity or side effects from the procaine solution would be expected with injections totaling less than 20 cc's at any one time. If the solution contains a vasoconstrictor, less than about 1.5 cc's of solution should be injected into any phalanx at one time to avoid shutting off blood circulation to the phalanx.

No further treatment of the warts is necessary or desirable after injection. For example, surgical excision of the injected wart after injection destroys the effectiveness of the procaine, since the required time to generate the necessary immune reaction is unavailable. A minimum of 2 weeks without any additional treatment is essential.

Progress of the warts after injection appears to vary with the individual treated and the formulation of treating solution. For example, procaine solutions containing a vasoconstrictor appear to resolve the warts more quickly than solutions not containing a vasoconstrictor. For vasoconstrictor-containing solutions, typically about two to four weeks after injection, the injected wart develops a redness and inflammation around its base. The redness may persist for anywhere from 5 to 20 days, and then subsides. The warts then change character to a dry and crusty appearance, and ultimately slough off in 2-4 months after the initial injection. For treating solutions not containing a vasoconstrictor, up to 6 months have been required for some cases. Very occasionally, the initial injection may not induce the necessary reaction, in which case one or more additional injection attempts may be made in the same or a new site. It is noted that a second injection is most commonly required in persons with allergies.

Although the mechanism is not understood, it has been hypothesized that warts have an ability to effectively mask the existence of the causative virus from the normal body reactions. For this reason, the body does not generate the necessary antibodies and antigens to combat the virus. The injection of procaine appears to break down the ability of the wart virus to mask its presence from the body's normal immune reactions. This procedure would explain the redness at the base of the wart several weeks after injection, indicating the presence of sensitization, and would also explain the fact that all of the warts on the body are cured by a single injection site. This mechanism would also explain the fact that the warts are not known to return after treatment, indicating development of a permanent immunity to the causative virus.

The solution used for injection preferably comprises procaine in the amount of from about 0.1% wt to about 10% wt, more preferably from 0.5-4% wt, in aqueous solution. The solution also preferably contains an effective amount of a vasoconstrictor, many of which are derivatives or analogs of phenylethylamine, such as epinephrine, levarterenol, arterenol, phenylephrine (Neo-Synephrin) or nordefrin (3,4 dihydroxy-phenyl-propanolamine, levo- or racemic). A vasoconstrictor retards absorption of the procaine in the tissues, thus prolonging its molecular existence. Procaine, which itself is a vasodilator, is easily and rapidly hydrolyzed to paraaminobenzoic acid and diethylaminoethanol in the tissues. The concentration of vasoconstrictor must be sufficient to allow vasoconstriction activity, and will depend on the particular vasoconstrictor selected. Generally concentration between about 0.005 and about 0.5 milligrams per milliliter of solution are adequate. Selection of an appropriate concentration is well within the skill of the art, using the same criteria as is used in formulating anesthetic solutions; guidance may be found in Chapter Seven of Monheim, "Local Anesthesia and Pain Control in Dental Practice", published by the Mosby Company, 1957.

The wart-treating solution may also contain additional components such as known local anesthetics such as propoxycaine hydrochloride and tetracaine hydrochloride, or other materials not harmful to the body, such as sodium chloride.

Since procaine is only slightly water-soluble, the active solution is best prepared from a water-soluble salt of procaine, especially a water-soluble acid salt such as the hydrochloride salt which is readily commercially available. These salts are readily water-soluble, and have a pH in solution of between 4 and 5. Any salt which is water-soluble and which decomposes in the tissues without harmful effects to the body may be used. When the term "procaine" is used herein in connection with a solution, it is understood to include any solubilized form of procaine, including acid salts such as the hydrochloride.

The invention is illustrated by means of the following examples. Solutions used in Examples I–V are as follows:

| SOLUTION A | |
|---|---|
| Compound | % wt |
| procaine hydrochloride | 2 |
| propoxycaine hydrochloride | 0.4 |
| levo-nordefrin | 0.005 |
| sodium chloride | 0.3 |
| acetone sodium bisulfate less than | 0.2 |
| water | balance |

SOLUTION B

-continued

| Compound | % wt |
| --- | --- |
| procaine hydrochloride | 2.0 |
| propoxycaine hydrochloride | 0.4 |
| levarterenol (as bitartrate monohydrate) | 0.0033 |
| sodium chloride | 0.3 |
| acetone sodium bisulfite less than | 0.2 |
| water | balance |

EXAMPLE I

The patient, a 42 year old caucasian, had a severe outbreak of warts on his hands and had been to dermatologists in several cities. At least 30 very large filiform warts existed. Prior treatments, including irradiation, were completely ineffective, and the patient indicated his job as a meat cutter to be in jeopardy because of the unattractive appearance of his hands.

After consulting a dermatologist, about 3.5 cc's of Solution A was injected around the periphery of and directly into a large wart on the right medial aspect of the right arm about three inches above the wrist. No other wart sites were injected. Multiple injections were made at the one site until the wart appeared to be raised up from the volume of solution beneath it.

In 90 days after the injection, about half of the warts had fallen off, and the rest appeared to be less integral with the skin. A slight redness appeared about the periphery of the remaining warts. After an additional 60 days, all of the remaining warts had disappeared without scarring. The only evidence of the warts was a slight lightness in skin pigment. The warts have not recurred. At present time there is no redness of skin, discernable scars, or other identification of past locations of warts.

EXAMPLE II

The patient, a 42 year old negro, had about 20 warts on his hands and fingers which had been present for several years. Approximately 3 cc's of Solution B was injected in and around the periphery of a wart on the first finger of the right hand. At the end of 60 and 90 days, no change had taken place. A different wart site, located on another finger was injected in a manner similar to the first injection. At the end of 60 days, no change had taken place, and the second wart site was again injected with about 3 cc's of the solution. After 60 days, the warts had changed character and were raised and dry but had not fallen off. In another 60 days, about half of the warts had fallen off, and after an additional 90 days, the remainder had disappeared. Only a slight lightness in pigment remained where the warts had been.

EXAMPLE III

An 18 year old caucasian patient having a large filiform wart that had existed for years on his right thumb was injected according to the invention with 3.5 cc's of Solution A. At the conclusion of the injection, the wart was raised and completely blanched and penetrated with solution. After 60 days, the wart had a red periphery, as if a reaction were taking place at its base. After an additional thirty days, the wart had fallen off. Ninety days later, the wart site was invisible.

EXAMPLE IV

The patient had multiple warts on both hands which had been present for years and which were steadily increasing in size and number. The largest and ugliest wart, on the left forefinger, was injected with 3.5 cc's of Solution A. After injection, the wart was completely whitened from the solution.

After 90 days, about six of the 12-15 warts had fallen off. After additional 180 days, all of the warts had disappeared, with the only residual appearance being a very slight pigment lightness.

EXAMPLE V

A white male, age 14, had a severe wart growth on his left elbow and a plantar wart on his left foot. About 2 cc's of Solution B was injected peripherally under and into the wart on the elbow. Within three months, both the wart on his elbow and the plantar wart had fallen off.

In addition to successful use on humans, the treatment of the invention is useful on animals. Treatments identical to the treatment described herein have satisfactorily removed warts from dogs, and would be expected to be successful for any warm-blooded mammal having warts.

A number of experiments were also conducted with a procaine solution not containing a vasoconstrictor. Solution C, a standard solution commercially available from Abbott Laboratories, used in all of the following Examples VI-XIX, is as follows:

| SOLUTION C | |
| --- | --- |
| Compound | % wt |
| procaine hydrochloride, USP | 2.0 |
| sodium bisulfite | 0.1 |
| water | balance |

EXAMPLE VI

The patient, a boy age 10, had moderate multiple warts on his hands which had been present for about 2 years. A single injection of a wart on the right hand resulted in complete resolution in about 6 months.

EXAMPLE VII

The patient was a 12 year old female having severe warts which had been present for about 24 months on both hands and knees. Prior treatment with liquid nitrogen and electrosurgery had no positive effect. After injection of one wart, in accord with the invention, all warts completely resolved without scarring in 4 months.

EXAMPLE VIII

The patient, a five year old boy, had severe warts on his hands, arms and face. The warts had been present for 24 months and had been treated with liquid nitrogen and with a 2% salicylic acid in vergo cream without success. A single wart on the left hand was injected in accord with the invention. All warts on the body resolved within 6 months of treatment.

EXAMPLE IX

The patient, a 37 year old male, had a single *plantar verruca* on his left sole. Prior treatment with 40% salicylic acid plasters was ineffective. The lesion had been present for about 36 months. A single injection of 2% procaine intralesionally resolved the wart within 6 months.

EXAMPLE X

The patient, a 13 year old female, had multiple severe warts on the right hand. Previous therapy with liquid nitrogen was ineffective. A single injection with procaine in accord with the invention resolved all of the warts within 3 months.

EXAMPLE XI

The patient, a 7 year old male, had moderate multiple verruca on the left hand. Previous liquid nitrogen therapy had no positive results. A single injection in accord with the invention resolved all of the warts within 3 months.

EXAMPLE XII

An 8 year old male had had severe multiple warts on his hands and face for 4 years. Prior treatment with liquid nitrogen and 2% salicylic acid in vergo cream was not effective. A single wart was injected with 2% procaine solution intralesionally. Complete resolution of all of the warts occurred within 5 months.

EXAMPLE XIII

A 15 year old female had severe multiple warts on her hands and the sole of her right foot. Prior treatment of 40% salicylic acid plaster to the plantar warts was not effective. A single wart on the left hand was treated in accord with the invention. All of the warts on the body resolved in about 3 months.

EXAMPLE XIV

The patient, an 8 year old boy, had severe multiple warts on his hands which had endured for approximately 18 months. Prior therapy with liquid nitrogen and 2% salicylic acid in vergo cream did not have positive results. Intralesional injection of a single wart caused resolution of all of the warts within 5 months.

EXAMPLE XV

An 18 year old male patient had a single wart on the right index finger which had been present for about 12 months. Injection according to the invention resolved the wart without scarring within 6 weeks.

EXAMPLE XVI

A 12 year old female patient had severe warts on her left hand and on her lips. A single injection of a wart on her left hand caused resolution of all warts within 3 months.

EXAMPLE XVII

A 9 year old female patient had a single large wart on her left knee. A single injection in accord with the invention resolved the wart within 4 months.

EXAMPLE XVIII

A 20 year old female patient had moderate warts in the area of her left hand. A single injection in accord with the invention completely cleared all of the warts within 5 weeks.

EXAMPLE XIX

A female patient, age 28, had moderate warts on both hands which had been present for about 18 months. Prior liquid nitrogen treatment was ineffective. A single injection of a wart on the right hand resolved all of the warts within about 5 weeks.

I claim:

1. A method of treating warts causing their remission which consists of injecting directly into the wart, under pressure, until at least part of the wart structure is physically destroyed and bleeding occurs, from about 0.5 to about 5 cc's of an aqueous solution comprising from about 0.1% to about 10% by weight of procaine, and allowing the treated wart to remain in place without surgical treatment for at least two weeks.

2. The method of claim 1 wherein the treating solution contains an effective amount of a vasoconstrictor.

3. The method of claim 1 wherein the amount of treating solution injected is from about 1 to about 1.5 cc's.

4. The method of claim 1 wherein the injection is continued under pressure until the tissue beneath the wart turns white, and solution spurts out from the wart.